United States Patent [19]

Bowling

[11] Patent Number: 5,532,254
[45] Date of Patent: Jul. 2, 1996

[54] MODULATION OF CALCIUM CHANNELS USING BENZOTHIOPHENES

[75] Inventor: Nancy L. Bowling, Greenfield, Ind.

[73] Assignee: Eli Lilly and Company, Indianapolis, Ind.

[21] Appl. No.: 485,317

[22] Filed: Jun. 7, 1995

[51] Int. Cl.$^6$ .................................................. A01N 43/40
[52] U.S. Cl. .................. 514/320; 544/146; 546/202; 548/523; 548/525; 549/44; 549/52; 549/53; 549/54; 562/843; 562/868
[58] Field of Search .............................. 514/320; 548/525; 548/523; 544/146; 546/202; 549/44, 52, 53, 54; 562/843, 868

[56] References Cited

U.S. PATENT DOCUMENTS

| | | | |
|---|---|---|---|
| 4,133,814 | 1/1979 | Jones et al. | 548/525 |
| 4,380,635 | 4/1983 | Peters | 546/202 |
| 4,418,068 | 11/1983 | Jones | 424/267 |

FOREIGN PATENT DOCUMENTS 0652000  5/1995  European Pat. Off. .

OTHER PUBLICATIONS

Collins et al., "Cardiovascular Protection by Oestrogen—A Calcium Antagonist Effect?", *Lancet*, 341, 1264–65 (1993).
Jiang et al., "Endothelium–Independent Relaxation of Rabbit Coronary Artery by 17β–Oestradiol In Vitro", *Br. J. Pharmacol.*, 104, 1033–37 (1991).
Stice et al., "Interaction of 4-Hydroxylated Estradiol and Potential–Sensitive $Ca^{2+}$ Channels in Altering Uterine Blood Flow during the Estrous Cycle and Early Pregnancy in Gilts", *Biology of Reproduction*, 36, 369–75 (1987).
Batra, "Influence of Chronic Oestrogen Treatment on the Density of Muscarinic Cholinergic Receptors and Calcium Channels in the Rabbit Uterus", *J. Endocrin.*, 125, 185–188 (1990).
Wren, "The Effect of Oestrogen on the Female Cardiovascular System", *Med. J. of Australia*, 157, 204–208, (1992).
Zhang et al., "Sexual Dimorphism of Vascular Smooth Muscle Responsiveness is Dependent on Anions and Estrogen", *Steroids*, 56, 524–526 (1991).
Kanis, American Journal of Medicine "Treatment of Osteoporosis in Elderly Women". (1995) pp. 60–66.

Primary Examiner—James J. Seidleck
Assistant Examiner—Terressa Mosley
Attorney, Agent, or Firm—Janelle D. Strode; James P. Leeds; David E. Boone

[57] ABSTRACT

A method for modulating calcium channels, increasing the density of calcium channels in vascular and cardiac tissue with no changes in inotropic or pressor response, comprising administering to a warm-blooded animal in need thereof a pharmaceutically-effective amount of a compound having the formula

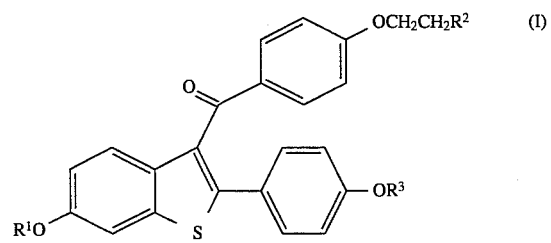

wherein $R^1$ and $R^3$ are independently hydrogen, $C_1$–$C_4$ alkyl, —CO—($C_1$–$C_6$ alkyl), or —$CH_2$Ar, —CO—Ar, wherein Ar is phenyl or substituted phenyl;

$R^2$ is selected from the group consisting of pyrrolidine, hexamethylenemino, and piperidino; or a pharmaceutically-acceptable salt thereof.

8 Claims, No Drawings

MODULATION OF CALCIUM CHANNELS USING BENZOTHIOPHENES

BACKGROUND OF THE INVENTION

This invention relates to the discovery that a group of 2-aryl-3-aroylbenzo[b]thiophenes are effective in modulating calcium channels, increasing the density of calcium channels in vascular and cardiac tissue, with no changes in inotropic or pressor response.

Replacement therapy with estrogen is generally acknowledged to produce beneficial effects on the cardiovascular system in postmenopausal women. See Knopt, *Obstet. Gynecol.*, 72 23s–30s (1988). In postmenopausal women who receive estrogens, the cardiovascular mortality rate is reduced by about 30% to about 50%, and the cerebrovascular mortality rate is reduced by about 50%. See Stampfer et al., *N. Engl. J. Med.*, 325, 756–762 (1991). Although these beneficial cardiovascular effects may involve alterations in lipid profile, recent data suggests that estrogen may also have beneficial effects on the vascular responses of atherosclerotic coronary arteries. See Gisclard et al., *J. Pharmacol. and Experimental Therapeutics* 244, 19–22 (1988); Williams et al., *Circulation*, 81, 1680–1687 (1990); Gangar et al., *Lancet*, 388, 839–842 (1991); and Williams et al., *JACC*, 20, 452–457 (1992). Both endothelial-independent and endothelial-dependent effects of estrogen have been described in vascular tissue. See Jiang et al., *Br. J. Pharmacol.*, 104, 1033–1037 (1991); Jiang et. al., *American Journal of Physiology*, 32, H271–H275 (1992); Cheng and Gruetter, *European Journal Of Pharmacol.*, 215, 171–176 (1992); Mügge et al., *Cardiovas. Res.*, 27, 1939–1942 (1993); Salas et al., *European Journal of Pharmacol.*, 258, 47–55 (1994); Williams et al., *Circulation*, 81, 1680–1687 (1990); Cheng et al., *Life Sciences*, 10, 187–191 (1994); Gilligan et al., *Circulation*, 89, 2545–2551 (1994); and Reis et al., *Circulation*, 89, 52–60 (1994). Several reports have also suggested that the vasodilating effects of estradiol and/or its ability to attenuate contractile responses may be mediated by inhibition of calcium influx via voltage dependent calcium channels. See Jiang et al., *Br. J. Pharmacol.*, 104, 1033–1037 (1991); Jiang et. al., *American Journal of Physiology*, 32, H271–H275 (1992); Collins et al., *Lancet*, 341, 1264 (1993); Muck et al., *Med. Sci. Res.*, 22, 19 (1994); and Salas et al., *European Journal of Pharmacol.*, 258, 47–55 (1994). Others have postulated that estradiol may enhance cyclic AMP and cyclic GMP content, or increase ATP-sensitive potassium channels. See Mügge et al., *Cardiovas. Res.*, 27, 1939–1942 (1993); Sudhir et al., *Am. Heart J.*, 129, 726–732 (1995).

The 2-aryl-3-aroylbenzo[b]thiophene compounds that are used in the methods of this invention were first developed by Jones and Suarez as anti-fertility agents. See U.S. Pat. No. 4,133,814 (issued Jan. 9, 1979). These compounds are generally useful in suppressing the growth of mammary tumors. Jones later found that a group of these compounds are particularly useful for antiestrogen and antiandrogen therapy, especially in the treatment of mammary and prostatic tumors. See U.S. Pat. No. 4,418,068 (issued Nov. 29, 1983). One of these compounds, 6-hydroxy-2-(4-hydroxyphenyl)- 3-[4-(2-piperidinoethoxy)benzoyl]benzo[b]thiophene was clinically studied for the treatment of breast cancer. This compound is called raloxifene, formerly keoxifene.

SUMMARY OF THE INVENTION

This invention provides methods for modulating calcium channels, increasing the density of calcium channels in vascular and cardiac tissue with no changes in inotropic or pressor response, comprising administering to a warm-blooded animal in need thereof an effective amount of a compound of the formula

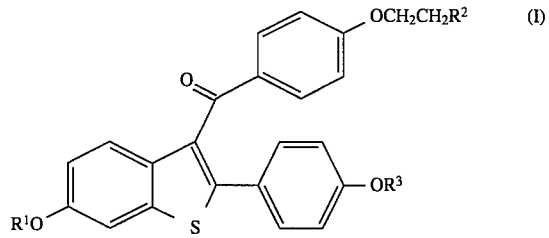

wherein $R^1$ and $R^3$ are independently hydrogen, $C_1$–$C_4$ alkyl, —CO—($C_1$–$C_6$ alkyl), —$CH_2$Ar, or —CO—Ar, wherein Ar is phenyl or substituted phenyl;

$R^2$ is selected from the group consisting of pyrrolidino, hexamethyleneimino, and piperidino; or a pharmaceutically-acceptable salt thereof. The present invention also provides the use of the formula I compounds, or pharmaceutically-acceptable salts thereof, for the manufacture of a medicament for modulating calcium channels in vascular and cardiac tissue.

DETAILED DESCRIPTION OF THE INVENTION

The present invention concerns the discovery that a select group of 2-aryl-3-aroylbenzo[b]thiophenes (benzo[b]thiophenes), the compounds of formula I, are effective in modulating calcium channels, increasing the density of calcium channels in vascular and cardiac tissue, with no changes in inotropic or pressor response. Therefore, the present invention provides methods for modulating calcium channels in vascular and cardiac tissue. One aspect of the invention is a method for treating cardiac disorders, including but not limited to variant angina, exertional angina, unstable angina, ischemia-reperfusion injury to the myocardium, and arrhythmias. Another aspect is a method for treating cerebral vascular disorders, including but not limited to cerebral vasospasm due to arterial rupture, stroke, and migraine headaches. Another aspect is a method for treating renal disorders by increasing renal clearance due to increases in renal blood flow, useful for slowing of renal failure. Another aspect is a method for treating gastrointestinal disorders, including but not limited to diseases related to diarrhea, such as IBS and IBD, diarrhea predominant. The therapeutic treatments provided by this invention are practiced by administering to a warm-blooded animal in need thereof a pharmaceutically-effective amount of a compound of formula I or a pharmaceutically-acceptable salt thereof.

In the above formula, the term "$C_1$–$C_6$ alkyl" represents a straight, cyclic, or branched alkyl chain having from one to six carbon atoms. Typical $C_1$–$C_6$ alkyl groups include methyl, ethyl, n-propyl, isopropyl, n-butyl, isobutyl, sec-butyl, t-butyl, n-pentyl, isopentyl, n-hexyl, cyclopropyl, cyclobutyl, cyclopentyl, cyclohexyl, and the like. The term "$C_1$–$C_4$ alkyl" represents a straight or branched alkyl chain having one to four carbon atoms. Typical $C_1$–$C_4$ alkyl groups include methyl, ethyl, n-propyl, isopropyl, n-butyl, secbutyl, isobutyl, and t-butyl.

The term "Ar" represents groups such as phenyl and substituted phenyl. The term "substituted phenyl", as used herein, represents a phenyl group substituted with one or more moieties chosen from the group consisting of halogen, hydroxy, cyano, nitro, $C_1$–$C_4$ alkyl, $C_1$–$C_4$ alkoxy, acetyl, formyl, trichloromethyl, or trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 4-cyanophenyl, 4-methylphenyl, 4-ethylphenyl, 4-methoxyphenyl, 4-propylphenyl, 4-n-butylphenyl, 4-t-butylphenyl, 3-fluoro-2-methylphenyl, 2,3-difluorophenyl, 2,6-difluorophenyl, 2,6-dimethylphenyl, 2-fluoro- 5-methylphenyl, 2,4,6-trifluorophenyl, 2-trifluoromethylphenyl, 2-chloro-5-trifluoromethylphenyl, 3,5-bis(trifluoromethyl)phenyl, 2-methoxyphenyl, 3-methoxyphenyl, 3,5-dimethoxyphenyl, 4-hydroxy-3-methylphenyl, 3,5-dimethyl- 4-hydroxyphenyl, 2-methyl-4-nitrophenyl, 4-methoxy-2-nitrophenyl, 2,4-dinitrophenyl, and the like. The term "$C_1$-$C_4$ alkoxy" represents groups such as methoxy, ethoxy, n-propoxy, isopropoxy, n-butoxy, t-butoxy, and the like. The term "halogen" represents fluoro, chloro, bromo, and iodo.

The term "pharmaceutically-effective amount" is used herein to represent an amount of the formula I compound that is capable of increasing the density of calcium channels in vascular and cardiac tissue. The particular dose of the formula I compound will of course be determined by the particular circumstances surrounding the case, including the compound administered, the route of administration, the particular condition treated, and similar considerations.

The term "modulating", as used herein, represents an increase in the density of calcium channels in vascular and cardiac tissue, with no changes in inotropic or pressor response.

The term "warm-blooded animal", as used herein, inlcudes humans; companion animals, such as dogs and cats; and domestic animals, such as horses, cattle, sheep, swine, goats and chickens. Preferably, the warm-blooded animal is a human or companion animal. More preferably, the warm-blooed animal is a human.

While all the formula I compounds are useful for modulating calcium channels in vascular and cardiac tissue, certain compounds are preferred. Preferably, $R^1$ and $R^3$ are independently hydrogen, $C_1$-$C_4$ alkyl, —CO—($C_1$-$C_6$ alkyl), or benzyl, and $R^2$ is piperidino or pyrrolidino. Representative compounds from this preferred group include 6-hydroxy-2-(4-hydroxyphenyl)- 3-[4-(2-pyrrolidinoethoxy)benzoyl]benzo[b]thiophene, 6-methoxy-2-(4-methoxyphenyl)-3-[4-(2-piperidinoethoxy)benzoyl]benzo[b]thiophene, 6-acetoxy-2-(4-acetoxyphenyl)- 3-[4-(2-pyrrolidinoethoxy)benzoyl]benzo[b]thiophene, and 6-benzyloxy-2-(4-benzyloxyphenyl)-3-[4-(2-piperidinoethoxy)benzoyl] benzo[b]thiophene.

More preferably, $R^1$ and $R^3$ are independently hydrogen or $C_1$-$C_4$ alkyl, and $R^2$ is piperidino or pyrrolidino. Representative compounds from this more preferred group include 6-hydroxy-2-(4-hydrophenyl)-3-[4-(2-pyrrolidinoethoxy)benzoyl] benzo[b]thiophene, 6-hydroxy-2-(4-hydroxyphenyl)- 3-[4-(2-piperidinoethoxy)benzoyl]benzo[b]thiophene, 6-methoxy-2-(4-methoxyphenyl)-3-[4-(2-pyrrolidinoethoxy)benzoyl]benzo[b]thiophene, and 6-methoxy-2-(4-methoxyphenyl)- 3-[4-(2-piperidinoethoxy)benzoyl]benzo[b]thiophene. Most preferably, $R^1$ and $R^3$ are hydrogen and $R^2$ is piperidino. This most preferred compound is 6-hydroxy-2-(4-hydroxyphenyl)-3-[4-(2-piperidinoethoxy)benzoyl]benzo[b]thiophene.

The formula I compounds used in the methods of the present invention can be made according to established procedures, such as those described in U.S. Pat. Nos. 4,133,814, 4,418,068, and 4,380,635, all of which are incorporated by reference herein. In general, the process starts with 6-hydroxy-2-(4-hydroxyphenyl)benzo[b]thiophene. This starting compound is protected, acylated at C-3 with a 4-(2-aminoethoxy)benzoyl group, and optionally deprotected to form the formula I compounds. Examples of the preparation of such compounds are provided in the U.S. Patents discussed above.

The compounds used in the methods of this invention form pharmaceutically-acceptable acid and, wherein $R^1$ and/or $R^3$ is hydrogen, base addition salts with a wide variety of organic and inorganic acids and bases, including the physiologically-acceptable salts which are often used in pharmaceutical chemistry. Typical inorganic acids used to form such salts include hydrochloric, hydrobromic, hydriodic, nitric, sulfuric, phosphoric, hypophosphoric, and the like. Salts derived from organic acids, such as aliphatic mono- and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically-acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, and β-hydroxybutyrate, butyne-1,4-dioate, hexyne-1,6-dioate, caprate, caprylate, chloride, cinnamate, citrate, formate, fumarate, glycolate, heptanoate, decanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartrate, and the like. The most preferred salt is the hydrochloride salt.

The pharmaceutically-acceptable acid addition salts are typically formed by reacting a compound of formula I with an equimolar or excess amount of acid. The reactants are generally combined in an organic solvent such as methanol, diethyl ether, or benzene. The salt normally precipitates out of solution within about one hour to 10 days and can be isolated by filtration, or the solvent can be stripped off by conventional means.

Bases commonly used for formation of salts include ammonium hydroxide and alkali and alkaline earth metal hydroxides, carbonates, as well as aliphatic primary, secondary, and tertiary amines, and aliphatic diamines. Bases especially useful in the preparation of addition salts include ammonium hydroxide, potassium carbonate, methylamine, diethylamine, ethylenediamine, and cyclohexylamine. These salts are generally prepared by reacting a formula I compound, wherein $R^1$ and/or $R^3$ are hydrogen, with one of the above bases in an organic solvent, such as methanol, diethyl ether, or benzene. The salts are isolated as described in the preceding paragraph.

These pharmaceutically-acceptable salts generally have enhanced solubility characteristics compared to the compound from which they are derived, and thus are often more amenable to formulation as liquids or emulsions.

The formula I compounds are preferably formulated prior to administration such as in a pharmaceutical formulation comprising a compound of formula I and a pharmaceutically-acceptable carrier, diluent, or excipient. These pharmaceutical formulations are prepared by known procedures using well-known and readily available ingredients. In making these compositions, the active ingredient will usually be mixed with a carrier, diluted by a carrier, or enclosed within a carrier which may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example up to 10% by weight of active compound, soft and hard gelatin capsules, dermal patches, suppositories, sterile injectible solutions, and sterile packaged powders.

Some examples of suitable carriers, excipients, and diluents include lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cross-linked polyvinylpyrrolidone, cellulose or derivatives thereof, water syrup, methyl cellulose, methyl and propyl hydroxybenzoates, talc, magnesium sterate and mineral oil. The formulations can additionally include lubricating agents, wetting agents (e.g. surfactant), emulsifying and suspending agents, disintegrating agents, preserving agents, sweetening agents, or flavoring agents. Compositions of the inventions may be formulated so as to provide quick, sustained, or delayed release of the active ingredient after administration to the patient by employing procedures well known in the art.

The particular dosage of a compound of formula I required for modulating calcium channels in vascular and cardiac tissue, according to this invention, will depend upon the severity of the condition, the route of administration, and related factors that will be decided by the attending physician. Generally, effective daily doses will be from about 0.1 to about 1000 mg/day, and more typically from about 10 to about 100 mg/day. Such dosages will be administered to a subject in need thereof from once to about three times each day, or more often as needed to effectively treat the condition or symptom.

It is usually preferred to administer a compound of formula I in the form of an acid addition salt, as is customary in the administration of pharmaceuticals bearing a basic group, such as the piperidino group. For such purposes the following oral dosage forms are available.

FORMULATIONS

In the formulations which follow, "Active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene Capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene Capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene Capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene Capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of Active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The Active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 500°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of Active ingredient per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The Active ingredient is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

Illustrative compounds that can be used in the methods of the present invention are shown in Table 1.

TABLE 1

| Compound No. | $R^1$ and $R^3$ | $R^2$ | Form |
| --- | --- | --- | --- |
| 1 | —C(O)—C₆H₄—F (para) | piperidino | base |
| 2 | —C(O)—C₆H₄—F (para) | piperidino | HCl |
| 3 | —C(O)-cyclopropyl | piperidino | base |
| 4 | —C(O)-cyclopropyl | piperidino | HCl |
| 5 | —C(O)CH$_2$CH$_2$CH$_3$ | piperidino | base |
| 6 | —C(O)CH$_2$CH$_2$CH$_3$ | piperidino | HCl |
| 7 | —C(O)C(CH$_3$)$_3$ | piperidino | base |
| 8 | —C(O)C(CH$_3$)$_3$ | piperidino | HCl |
| 9 | —C(O)CH$_2$C(CH$_3$)$_3$ | piperidino | base |
| 10 | —C(O)CH$_2$C(CH$_3$)$_3$ | piperidino | HCl |
| 11 | —C(O)—C₆H₄—CH$_3$ (para) | piperidino | HCl |
| 12 | —C(O)—C₆H₅ | piperidino | base |
| 13 | H | piperidino | base |
| 14 | H | piperidino | HCl |
| 15 | H | pyrrolodino | base |
| 16 | H | pyrrolodino | HCl |
| 17 | H | hexamethyleneimino | HCl |

TABLE 1-continued

| Compound No. | $R^1$ and $R^3$ | $R^2$ | Form |
| --- | --- | --- | --- |
| 18 | CH$_3$ | piperidino | HCl |

The utility of the compounds of formula I is illustrated by the positive impact they have in at least one of the experiments described below.

Materials and Methods

Selection and dosing of rats were essentially as described by Sato et al. Sato et al., *J. Bone and Mineral Research*, 9, 715–724 (1994). Briefly, ovariectomized (ovex) virgin female rats (6 months old) were divided into 3 groups of 6, designated as: ovex; ethinyl estradiol (EE2, 0.1 mg/kg/day p.o.); and raloxifene (compound 14, 1.0 mg/kg/day p.o.). A fourth group of sham-operated females (sham) served as a second control. Doses of EE2 and 14 were selected for comparable effects on bone density parameters (Sato et al.); incidentally they produced similarly significant (P,0.05 vs ovex) effects at lowering total cholesterol (36±2 and 38±4 mg/dl, EE2 and 14, respectively, vs 85±7 and 87±7 mg/dl, ovex and sham, respectively). Sham and ovex rats were administered vehicle (100 μg/g body weight of 20% hydroxypropyl-S-cyclodextrin). Animals were dosed for 35 days and sacrificed by excess $CO_2$.

Hearts and aortas were carefully dissected, quickly frozen and stored at −70° C. if membranes were not prepared immediately. Microsomal membrane vesicles were isolated from 3–4 g minced hearts or aortas from each group as previously described. Jones et al., *J. Biol. Chem.*, 254, 530–535 (1979). Preparations were stored in 0.25M sucrose/30 mM histidine at −70° C. Binding studies using increasing concentrations of the calcium channel ligand [$^3$H] PN200-110 (0.01–4.0 nM) were done in 12×75 mm glass tubes (total volume 500 μl) at 23° C. for 2 h using 100 (heart) or 200 (aorta) μg protein per tube. Assays were terminated by rapid filtration onto Whatman GF/C filter paper. Assay (and wash) buffer was 50 mM Tris/HCl (pH 7.3), 1 mM EDTA and 12 mM $MgCl_2$. Nonspecific binding was defined as binding remaining in the presence of 1 μM nifedipine.

Radioligand binding affinity and receptor density were determined from saturation isotherm data using the nonlinear regression analysis program LUNDON-1. Lundeen and Gordon, in *Receptor Binding in Drug Research*, 31–49, 1986.

Cardiovascular hemodynamic parameters in response to BAY k 8644 were determined in pithed rats from each of the four groups (sham, ovex, EE2, and 14) as described by Hayes and Bowling with the following modifications: the drug was administered through the femoral vein; and direct measurement of left ventricular systolic blood pressure was obtained by inserting a small section of PE 90 tubing attached to a pressure transducer directly into the left ventricle. Hayes and Bowling, *J. Pharmacol. and Exp. Ther.*, 241, 861–869 (1987). Measurements were obtained of mean, systolic and diastolic blood pressure, heart rate, left ventricular systolic pressure and left ventricular dP/dt.

Results

EE2 and 14 effects on $Ca^{2+}$ channel binding ([$^3$H] PN-200–110) in cardiac and aortic tissues, and on in vivo hemodynamic responses to BAY k 8644 were determined and compared to ovex and sham controls. Whereas high affinity dihydropyridine binding sites ($B_{max}$) in cardiac and aortic tissues were significantly increased in EE2- and 14-treated rats compared to ovex rats, binding affinities ($K_d$)

were not significantly different among groups in either cardiac or aortic tissues.

| Treatment group | chol mg/dL | cardiac $B_{max}$ (fmol/mg) | [$^3$H]PN200-100 $K_d$ (pM) | aortic $B_{max}$ (fmol/mg) | $K_d$ (nM) |
|---|---|---|---|---|---|
| ovex (n = 5–7) | 85 ± 7 | 296 ± 51 | 200 ± 19 | 61 ± 15 | 1.0 ± 0.3 |
| sham (n = 4–6) | 87 ± 7 | 385 ± 76 | 188 ± 32 | 46 ± 14 | 2.5 ± 0.6 |
| EE2 (n = 5–7) | 36 ± 2* | 525 ± 65* | 204 ± 21 | 133 ± 26* | 2.5 ± 0.6 |
| Ralox (n = 4–5) | 38 ± 4* | 535 ± 80* | 171 ± 18 | 124 ± 18* | 1.3 ± 0.6 |

*$p < 0.05$ vs ovex

Despite the increase in $Ca^{2+}$ channel $B_{max}$, in vivo contractile, heart rate and pressor responses to BAY k 8644 in EE2-treated rats were not increased compared to those of ovex or sham controls. Thus increased $Ca^{2+}$ channel density did not result in a more sensitized response to the calcium channel agonist.

I claim:

1. A method for modulating calcium channels in vascular and cardiac tissue comprising administering to a warm-blooded animal in need thereof a pharmaceutically-effective amount of a compound having the formula

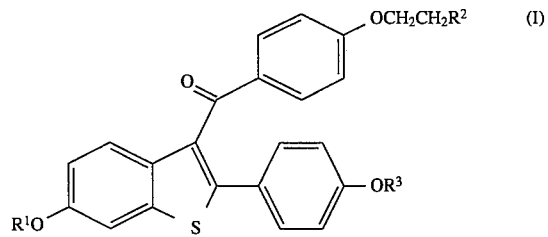

wherein $R^1$ and $R^3$ are independently hydrogen, $C_1$–$C_4$ alkyl, —CO—($C_1$–$C_6$ alkyl), or —CH$_2$Ar, —CO—Ar, wherein Ar is phenyl or substituted phenyl;

$R^2$ is selected from the group consisting of pyrrolidine, hexamethylenemino, and piperidino; or a pharmaceutically-acceptable salt thereof.

2. The method of claim 1 wherein $R^1$ and $R^3$ are independently hydrogen, $C_1$–$C_4$ alkyl, —CO—($C_1$–$C_6$ alkyl), or benzyl; and $R^2$ is piperidino or pyrrolidino.

3. The method of claim 2 wherein $R^1$ and $R^3$ are independently hydrogen or $C_1$–$C_4$ alkyl, and $R^2$ is piperidino or pyrrolidino.

4. The method of claim 3 wherein $R^1$ and $R^3$ are hydrogen and $R^2$ is piperidino or pyrrolidino.

5. The method of claim 4 wherein $R^2$ is piperidino.

6. The method of claim 5 wherein said pharmaceutically-acceptable salt is the hydrochloride salt.

7. The method of claim 4 wherein $R^2$ is pyrrolidino.

8. The method of claim 7 wherein said pharmaceutically-acceptable salt is the hydrochloride salt.

* * * * *